United States Patent [19]
Ryback et al.

[11] Patent Number: 5,176,145
[45] Date of Patent: Jan. 5, 1993

[54] METHOD FOR DIAGNOSING A PATIENT TO DETERMINE WHETHER THE PATIENT SUFFERS FROM LIMBIC SYSTEM DYSRHYTHMIA

[76] Inventors: Ralph S. Ryback, 11607 Springridge Rd., Potomac, Md. 20854; Elmer A. Gardner, 4545 42nd St., NW., Suite 204, Washington, D.C. 20016

[21] Appl. No.: 646,013

[22] Filed: Jan. 28, 1991

Related U.S. Application Data

[63] Continuation-in-part of Ser. No. 514,413, Apr. 25, 1990, abandoned.

[51] Int. Cl.⁵ .......................................... A61B 5/0476
[52] U.S. Cl. .................................................. 128/731
[58] Field of Search ........................ 128/731; 514/821

[56] References Cited

U.S. PATENT DOCUMENTS

| | | | |
|---|---|---|---|
| 4,533,346 | 8/1985 | Cosgrove et al. | 128/731 |
| 4,550,736 | 11/1985 | Broughton et al. | 128/731 |

OTHER PUBLICATIONS

Adamec et al., "Basic Science and Clinical Aspects of Procaine HCl As a Limbic System Excitant," Prog. Neuro-Psychopharmacol. & Biol. Psychiat., 1985, vol. 9, pp. 109-119, Permagon Press Limited.

Kellner et al., "Intravenous Procaine As a Probe of Limbic System Activity in Psychiatric Patients and Normal Controls," Biol. Psychiatry, 1987, vol. 22, pp. 1107-1126.

Adamec et al., "The Effects of Procaine HCl on Population Cellular and Evoked Response Activity Within the Limbic System of the Cat. Evidence for Differential Excitatory Action of Procaine in a Variety of Limbic Circuits," Prog. Neuropsychopharmacol. Biol. Psychiatry, 1987, vol. 11 (4), pp. 345-364.

Adamec et al., "Power Spectral Analysis of EEG Drug Response in the Kindled Rat Brain," Electroencephalogr. Clin. Neurophysiol., 1981, vol. 52(5), pp. 451-460.

Stark et al., "Analysis of Facial Displays and Verbal Report to Assess Subjective State in the Non-Invasive Detection of Limbic System Activation by Procaine Hydrochloride," Behav. Brain Res., 1982, Jan., vol. 4 (1), pp. 77-94.

Kling et al., "Neuroendocrine Effects of Limbic Activation by Electrical, Spontaneous and Pharmacological Modes: Relevance to the Pathophysiology of Effective Disregulation in Psychiatric Disorders," Prog. Neuropsychopharmacol. Biol. Psychiatry, 1987, vol. 11 (4), pp. 459-481.

Kellner, "Intravenous Procaine As a Probe of Limbic Systems Activity in Psychiatric Patients and Normal Controls," Biol. Psychiatry, 1987, Sep., vol. 22 (9), pp. 1107-1126.

Pollock, "The Kindling Phenomenon and a Clinical Application: The Procaine Test," The Psychiatric Journal of the University of Ottawa, vol. 10, No. 4, pp. 185-191, Dec. 1985.

Himmelhoch, "Cerebral Dysrhythmia, Substance Abuse, and the Nature of Secondary Affective Illness," Neuropsychiatry of Mood Disorders, Psychiatric Annals, 17 (11), Nov. 1987, pp. 710-727.

*Primary Examiner*—William E. Kamm
*Attorney, Agent, or Firm*—Pollock, Vande Sande & Priddy

[57] ABSTRACT

A patient is diagnosed to determine whether the patient has a limbic system dysrhythmia and capable of being treated by administration of an anticonvulsant medication by determining whether the patient exhibits symptoms in at least four groups out of twelve defined groups of symptoms. In addition, an electroencephalogram is studied for any focal abnormalities in the temporal parietal areas and, if there are none, the patient is administered a local anaesthetic, procaine, and the electroencephalogram is evaluated for omega band activity (30-50 Hz). A patient exhibiting either focal abnormalities in the temporal-parietal areas on the standard electroencephalogram or, after procaine, exhibiting omega band activity of at least about three times the baseline voltage above normal and exhibiting symptoms in at least four groups of the twelve groups of defined symptoms is diagnosed as having Limbic System Dysrhythmia and being capable of treatment by administering an anticonvulsant medication.

12 Claims, 3 Drawing Sheets

✻ = ANTERIOR TEMPORAL LEADS FILTERED
FOR OMEGA ACTIVITY (30-55 HZ.)

METHOD FOR DIAGNOSING A PATIENT TO DETERMINE WHETHER THE PATIENT SUFFERS FROM LIMBIC SYSTEM DYSRHYTHMIA

CROSS REFERENCES TO RELATED APPLICATIONS

The present application is a continuation-in-part of our copending U.S. Pat. application Ser. No. 07/514,413 filed Apr. 25, 1990 and entitled "Diagnostic Electroencephalogram Procedure."

DESCRIPTION

1. Technical Field

The present invention is concerned with a method for diagnosing a patient to determine whether the patient suffers from limbic system dysrhythmia and is capable of being successfully treated by administering anti-convulsant medication. In particular, the present invention is concerned with a diagnostic process that includes selection of patients with a certain constellation of symptoms and an electroencephalogram (EEG) analysis for determining increased activity in the omega band range (30-55 hertz).

2. Background Art

Diagnosing and attempting to treat a particular mental disorder requires a great deal of effort to first determine in what diagnostic group the patient should be characterized. However, it is often difficult to place a particular patient in a diagnostic group. Diagnosis of patients usually entail a thorough medical examination to determine whether the patient suffers from any physical conditions that may contribute to the cause of the mental disorder. Then, the patient is interviewed over a period of time. For many years various EEG tests have been used to detect any changes in a patient's brain waves. For the most part these EEG tests do not involve the omega band range. However, there have been some recent suggestions in the literature that using an electroencephalogram analysis in the omega wave band range produced by the administration of a local anaesthetic, procaine, and a series of intravenous doses of increasing amount could be useful as a clinical probe and could possibly predict good clinical response to carbamazepine. For example, see Adamec et al., Basic Science and Clinical Aspects of Procaine HCl as a Limbic System Excitant, *Prog. Neuro-psychopharmacol. & Biol. Psychiat.*, 1985, Vol. 9, pp. 109-119, Pergamon Press Limited and Kellner et al., Intravenous Procaine as a Probe of Limbic System Activity in Psychiatric Patients and Normal Controls, *Biol. Psychiatry*, 1987, Vol. 22, pp. 1107-1126. However, even with the use of EEG analysis, the ability to predict with any reasonable degree of success whether a patient would be a likely candidate for treatment was not possible from the above discussions. Moreover, the procedures required a plurality of intravenous doses of a local anaesthetic such as procaine in increasing amounts which is both extremely time consuming and quite uncomfortable if not disturbing for the patient.

Moreover, the ability to reasonably predict whether a patient would be successfully treated by a particular pharmaceutical cannot be underestimated, since an incorrect diagnosis could not only result in an ineffective treatment but one that might even be harmful to the patient.

Accordingly, it would be desirable to provide a diagnostic method that has a very high probability of success and is relatively easy to carry out.

SUMMARY OF INVENTION

The present invention is concerned with a method for diagnosing a patient to determine whether the patient suffers from limbic system dysrhythmia and can be successfully treated by administration of an anticonvulsant medication In accordance with the present invention, the patient is analyzed to determine whether the patient exhibits at least four symptoms from a group of twelve defined symptoms This group of symptoms includes mood change, particularly frequent, abrupt, fluctuating within one day or from day-to-day or week-to-week, along with swings in mood and occasionally only depression although rarely, chronic fluctuating depression; panic attacks which occur randomly and vary in intensity or having constant intense anxiety experienced as ego alien; rage reaction, often only intense anger and with or without behavioral concomitant, or varying degrees of anger provoked with only minor provocation, and uncontrollable, often experienced with vague or no recall of event; headache, focal or more generalized and bilateral, usually starting unilaterally or varying types of headaches either migraine in character, but more often tension like with muscle tenseness: addictive states consisting of alcohol dependency, bulimia, opiods, marijuana, hallucinogenics, prescription drug dependency, or smoking, the degree and constancy of the addictive state varying and occurring with or without accompanying behaviors of addictive state; learning disability, perceptual dysfunction—problems in integrating sensory input—usually visual, occasionally auditory, often subtle and covered by compensatory mechanisms or associated with problems of attention; paranoid episodes or paranoid thinking often intensified with stress or a general suspiciousness in ideation though not definitely paranoid; peripheral neuropathic signs, paresthesias or hypoesthesis—in one or more extremities—usually episodic; seizure-like phenomena including blackouts, trances or impaired consciousness, myoclonic twitches; self-destructive behavior, episodic—include cutting, burning, biting self, hitting self or the wall, or other objects seems to relieve the mental discomfort or pain; autoimmune-endocrine disorders—rheumatoid arthritis, lupus erythematosus, asthma, ileocolitis, hypothyroidism, menstrual irregularities and polycystic ovarian disorder; and antidepressant-stimulant response with excessive stimulation or manic-like response to antidepressant medications and stimulants.

In addition, an EEG is performed and evaluated for focal abnormalities in the temporal-parietal areas. If there are none a patient is administered a local anaesthetic, procaine, and evaluated for omega band activity (30-50 Hz.) of at least approximately three times the baseline voltage (for example, at least about 45 microvolts at a baseline voltage of about 15 microvolts) in the anterior temporal leads of the EEG. The patient who exhibits either focal abnormalities or omega band activity after local anaesthetic administration and has at least four of the above specified symptom groups is diagnosed as having limbic system dysrhythmia and is susceptible of being successfully treated by the administration of anticonvulsant medication.

In addition, the present invention is concerned with treating patients diagnosed by the procedure discussed above as having limbic system dysrhythmia by administering to said patients anticonvulsant medication.

BEST AND VARIOUS MODES FOR CARRYING OUT INVENTION

Figure 1A:
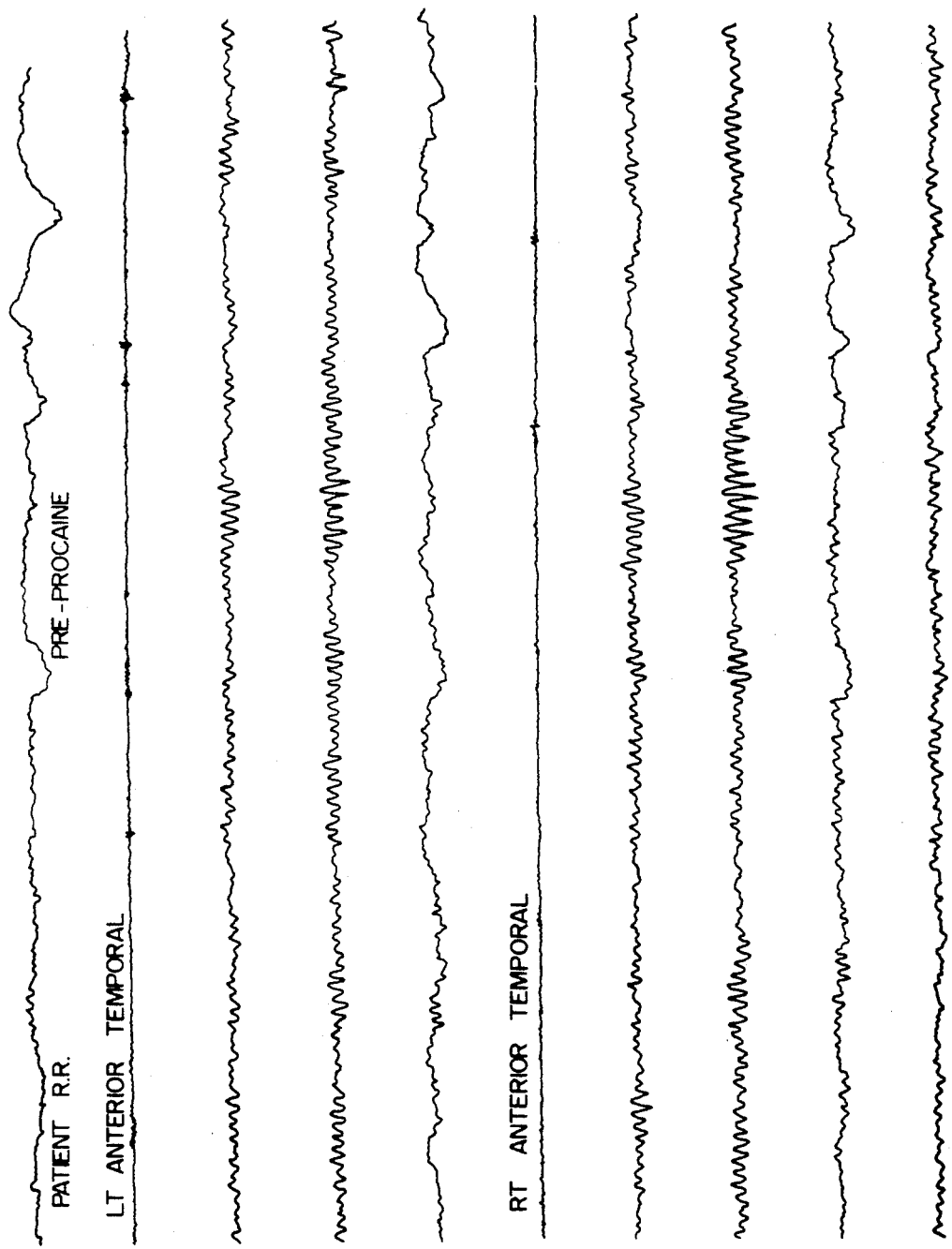
FIG. 1 is an EEG tracing before, during and after procaine activation.

In accordance with the present invention, a procedure that is relatively simple to carry out and is more universal than prior suggested diagnostic methods has been achieved. The diagnostic method of the present invention makes it possible to distinguish a category of patients that are most likely to show positive response to treatment with an anticonvulsant medication.

In accordance with the present invention, a patient suffering from a mental disorder is evaluated to determine whether the patient exhibits symptoms in at least four of the twelve groups of symptoms defined herein below.

Group 1 is referred to as rapid mood change which occurs frequently and abruptly and may fluctuate within one day or from day-to-day or week-to-week. The changes are often swings in mood but occasionally only depression.

Group 2 is diagnosed as panic attacks. The panic attacks are typically random but increase in frequency with stress. The intensity of the attacks vary and occasionally can be characterized as phobic reactions. Some of the patients have constant intense anxiety which is experienced as ego alien. Some of these patients have at least four of the following symptoms during an attack as defined in DSM III-R, 1987, pp. 139-140 for panic disorder:

1. shortness of breath (dyspnea) or smothering sensations
2. dizziness, unsteady feelings, or faintness
3. palpitations or accelerated heart rate (tachycardia)
4. trembling or shaking
5. sweating
6. choking
7. nausea or abdominal distress
8. depersonalization or derealization
9. numbness or tingling sensations (paresthesias)
10. flushes (hot flashes) or chills
11. chest pain or discomfort
12. fear of dying
13. fear of going crazy or of doing something uncontrolled Group 3 symptom is referred to as rage reaction. It often involves intense anger and no behavioral concomitant. The degree of anger is variable and is usually unprovoked or with only slight or minor provocation. The reaction is usually uncontrollable, sudden and ego alien. Often there is no or at most vague recall of the event.

Group 4 symptom is headaches which typically are focal, occasionally more generalized and bilateral, usually starting unilaterally. The type of headaches varies; it may be migraine in character with aura, or, more often, the headaches are tension-like with muscle tenseness.

Group 5 symptom is addictive states with at least one of these addictions bulimia, compulsive eating, single food addictions, alcoholism, marijuana, hallucinogen and other street drug dependency, prescription drugs or smoking. The degree and constancy of the addictive state varies but often is ascribed to necessity in controlling mood. Such can occur with or without accompanying behaviors of addictive state.

Group 6 symptom is Learning Disability characterized by perceptual dysfunctions. This symptom is usually identified by problems in integrating sensory input which impairs or delays comprehension and is typically visual though occasionally auditory. This symptom is often subtle and masked by compensatory mechanisms. There may also be problems with attention contributing to the disorder with some patients having a number of the symptoms or the complete criteria (at least eight of the following fourteen symptoms for at least six months) defined in DSM III-R, 1987, pp. 56-57 for Attention Deficit and Hyperactivity Disorder as follows:

1. often fidgets with hands or feet or squirms in seat (in adolescents, may be limited to subjective feelings of restlessness)
2. has difficulty remaining seated when required to do so
3. is easily distracted by extraneous stimuli
4. has difficulty awaiting turn in games or group situations
5. often blurts out answers to questions before they have been completed
6. has difficulty following through on instructions from others (not due to oppositional behavior or failure of comprehension), e.g., fails to finish chores
7. has difficulty sustaining attention in tasks or play activities
8. often shifts from one uncompleted activity to another
9. has difficulty playing quietly
10. often talks excessively
11. often interrupts or intrudes on others, e.g., butts into other children's games
12. often does not seem to listen to what is being said to him or her
13. often loses things necessary for tasks or activities at school or at home (e.g., toys, pencils, books, assignments)
14. often engages in physically dangerous activities without considering possible consequences (not for the purpose of thrill-seeking), e.g., runs into street without looking Group 7 symptom is Paranoid episodes or Paranoid Thinking. This is often intensified with stress. It may be general suspiciousness though not definitely paranoid.

Group 8 symptom is Peripheral Neuropathic signs which are typically paresthesias, myoclonic twitches or hypoesthesia of hands, feet or one or more extremities with tingling or numbness. It is usually episodic.

Group 9 symptom is Seizure-like Phenomena such as blackouts, trances and impaired consciousness (e.g. "spacing or zoning out").

Group 10 symptom is Self-Destructive Behavior episodes such as cutting, burning, biting or hitting oneself or the wall or other objects. Normally, these episodes seem to relieve the mental pain or discomfort of the patient.

Group 11 symptom is Autoimmune-Endocrine Disorders. These include rheumatoid arthritis, lupus erythematosus, asthma, ileocolitis, hypothyroidism, menstrual irregularities or polycystic ovarian disorder.

Group 12 symptom is Antidepressant-Stimulant Response typically exhibited by excessive stimulation or maniclike response to antidepressant medications and stimulants.

Figure 1B:
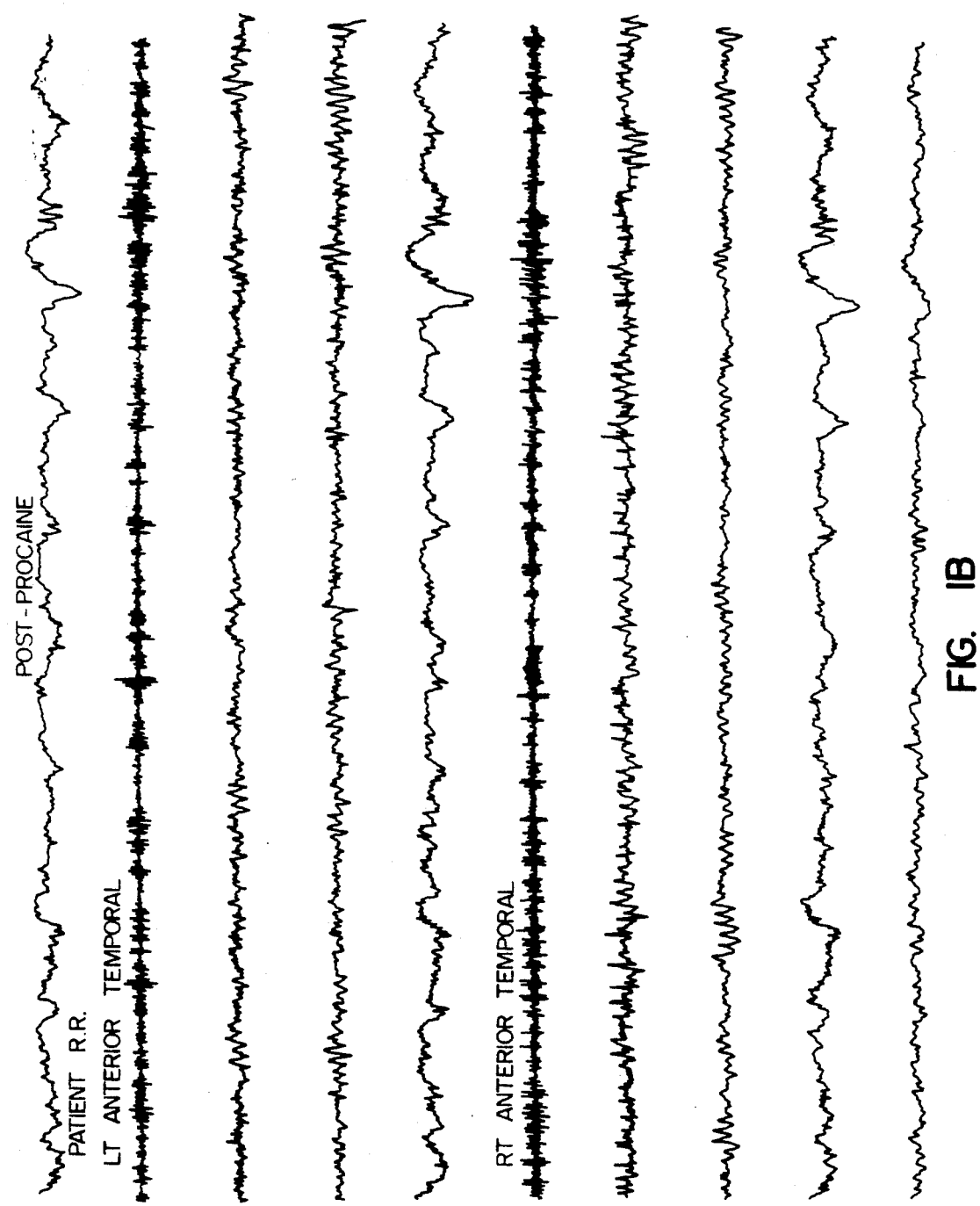
Figure 2:
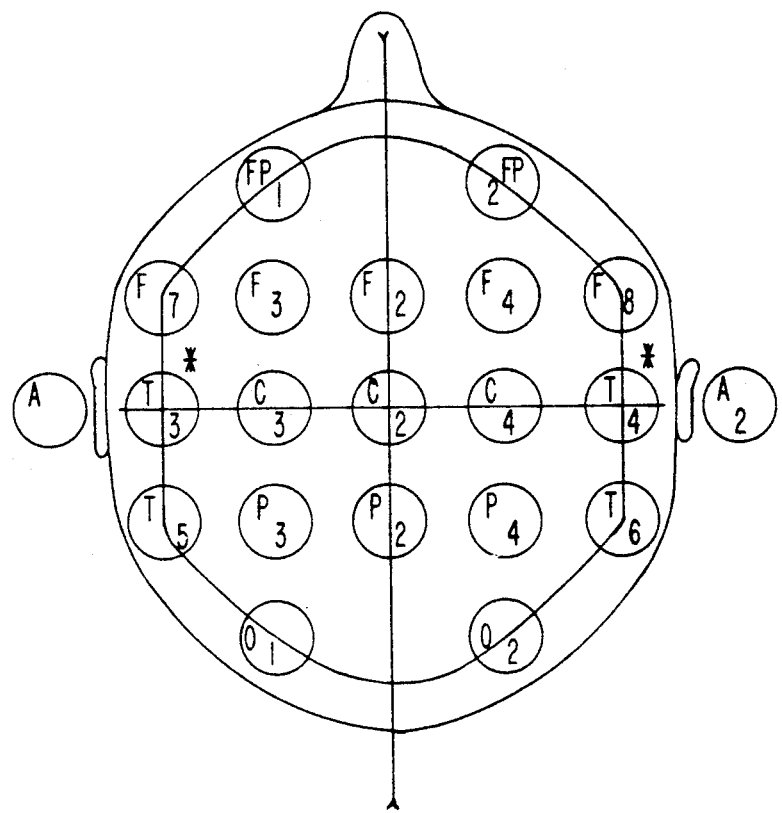
FIG. 2 illustrates the standard placement of leads.

In addition to exhibiting symptoms in at least four groups out of the above twelve symptom groups, a standard electroencephalogram is performed looking for focal abnormalities in the temporal-parietal areas. If there are none, the patient is also administered a local anaesthetic, procaine, with an EEG evaluation for omega band activity (30-50 Hz.) approximately three times the baseline voltage in the anterior temporal leads of the EEG (see FIG. 1). It has been found pursuant to the present invention that it is not necessary to administer increasing doses of the local anaesthetic to the patient but instead a one dose intravenous administration of 1.38 mg/kg of body weight in a volume of about 3-6 cc.

Patients that satisfy the above conditions are diagnosed as having Limbic System Dysrhythmia and are capable of successful treatment by administration of an anticonvulsant medication such as Tegretol (carbamazepine), Depakene or Depakote (valproic acid), or Klonopin (clonozepam) alone or in combination with an antidepressant or neuroleptic medication. Without the use of the anticonvulsant medication, the use of the antidepressant or neuroleptic medication is usually ineffective or may actually exacerbate (especially with antidepressants) the condition.

The anticonvulsant medication is generally administered in dosages providing a therapeutic range as defined for seizure control. The medication is given orally. Such ranges are well known, for instance, such can be found in the Physician's Desk Reference, 1988 Edition, Charles Baker, Medical Economics Company or obtained from the manufacturer of the anticonvulsant medication. In addition, in a number of cases, dosages can be reduced to about 50% of the therapeutic range for seizure control. The exact amount to be given to any particular patient can be determined by persons skilled in the art after being made aware of the present invention without undue experimentation.

The above diagnostic procedure has been established to be successful by testing and treatment carried out by the present inventors over the last several years on over 150 individuals suffering from mental disorder. Such evaluation has led to the ability to diagnose a subpopulation of patients having an Affective and other disorders that can be responsively treated by administration of an anticonvulsant medication. The characteristics of a group of 56 patients are presented in Tables I-III and a second group of 114 patients in Table IA-IIIA.

The following non-limiting examples are presented to illustrate the present invention:

EXAMPLE I

The patient is a male student who presents with the symptoms of dyscontrol, mood swings and sleep disruption becoming progressively worse in the past three years. The history revealed his father allegedly being explosive and very angry at times, a grandfather who had rages and a great-grandfather that was described as a tyrant. A medical history included sleep problems which existed for a prolonged period of time and an adverse response to Ritalin. The patient had been seen by multiple psychiatrists over the period of seven years and had multiple psychological and neuropsychological evaluations. The patient had also been through several private schools in each case being asked to leave because of his offensive and out of control verbal behavior.

The patient presented casually dressed with an excellent memory, oriented times three, showing good judgement except when overwhelmed, and of superior intellect. His affect was appropriate, his mood was slightly depressed and his cognition intact. He denied delusions and hallucinations as well as suicidal thoughts. Symptoms consistent with cerebral dysrhythmia included problems with integration such as having to talk his way through material in order to learn it and findings of relative visual and written processing problems with his strength being auditory processing. It was noted that the patient could not do the multiplication tables for several years. The patient also complained of headaches sometimes lasting several days which were emotionally upsetting. He experienced dyscontrol (feelings that he was going to lose control) which he found that he was able to control by watching TV or listening to heavy metal music. When upset, he would become "spaced out." The patient experienced panic attacks, described as "I can't breathe" which involved hyperventilation on several occasions. He denied any involvement with addictive substances, however, he did note that he had rapid mood changes in which he became intensely angry, became happy and then angry and back again. Some findings of mild paranoia (e.g., he would feel insanely jealous of a girlfriend resulting in behavior which was inappropriate). He noted some olfactory experiences, particularly related a repeating dream in which he would wake up smelling certain types of flowers sometimes for several nights in a row. The patient acknowledged sleep disruption which resulted in pacing or watching TV. He had difficulty falling asleep particularly if upset. The patient was directed to obtain a procaine activated EEG. The baseline EEG was normal. Procaine activation produced bilateral omega activity at a significant level which was much more marked on the right side or the nondominant hemisphere with some posterior spread. This was accompanied by sensory misperception and anxiety. The patient was begun on Tegretol in increasing dosages over a number of days. The patient and family noted he began sleeping more than eight hours per night versus the three or four that he had slept in the previous four years. He began feeling less paranoid, and began to feel "annoyed" rather than "angry." His Tegretol level was raised into the therapeutic range and the dose of Tegretol was spread out during the day. The patient was encouraged to learn some study habit techniques which he had never been able to learn before or take the time to do so. His school performance began to improve in areas such as math now that he was able to concentrate. His tutor was particularly impressed by the significant change in his behaviors. He began getting high 80's in math, where previously he had received 30's. His therapist noted that he was much more available psychologically to work in therapy as well as deal with his family. He began to confront his family about their erratic behaviors. Over the next few months the patient was able to leave a private school setting and enter public school. He has continued to do well and perform at a B average level at one of the finest high schools in this area whereas previously he had been getting C's or lower in all settings.

EXAMPLE II

The patient is a male student. His chief complaint was "trouble controlling my anger." The patient presented a history of having behavioral problems including vandalism, stealing cars, shooting out windows, being arrested for shoplifting, riding motorcycles without a helmet, etc. Prior to the 7th grade the patient was allegedly an excellent student and has continued to do well in IQ and performance tests. However, since then he had been dismissed from several private schools for smoking, stealing slips out of locked school offices, and breaking and entering. There was no family history of loss of control, other than an older brother who had problems with his temper. The patient related a medical history including a head injury this past Thanksgiving with no concussion. He noted trouble falling asleep, described as difficulty "shutting off my brain."

There was no history of previous psychiatric treatment, he was on no medication.

The patient presented in a jean jacket and slacks, seemed to have intact recent memory and was orientated times three. His judgement seemed to be poor by history and to be of average intelligence. His affect was that of a sad facies with depressed mood. His cognition was intact and he denied delusions, hallucinations or suicidal thoughts.

Symptoms consistent with an organic affective state or cerebral dysrhythmia included often not seeming to listen, acting before thinking, headaches, symptoms of dyscontrol, rapid mood changes with clenched jaws and fists, extremely distrustful and when intoxicated losing control and getting into fights. The patient had been previously tested elsewhere. An initial report suggested no evidence of learning disability, concentration or attention problems. Instead the focus of the report suggested the patient was easily frustrated and was depressed. The patient's parents were extremely anxious and they wished to initiate treatment prior to the EEG since the EEG could not be done for several weeks. A trial of Tegretol was initiated and increased into the therapeutic range. The patient acknowledged being somewhat more relaxed and being able to sleep slightly better, however, the sleep pattern continued to be irregular and the patient's rapid mood changes, explosiveness and distrustfulness continued. An EEG was done, the baseline EEG was normal and procaine activated EEG was normal.

The patient was admitted for inpatient evaluation. Psychological testing elsewhere indicated no psychopathology. However, intensive psychiatric interview revealed that the patient was experiencing voice commands, racing thoughts and flight of ideas. The patient was prescribed at first Lithium in increasing dosages and eventually also Trilafon. His racing thoughts decreased, and his paranoia diminished. The patient was stabilized on these two medications and was eventually discharged. He has stabilized and continues to be followed in an outpatient group. The patient has entered a private school where he has done fairly well. Improved communication with family members has occurred.

EXAMPLE III

The patient is a female who presents with a long history of various type of neurotic, panic or chronic anxiety disorders. As early as the 6th grade, the patient was felt to have a school phobia. She threatened at times to harm herself.

A history was obtained of rapid mood changes, panic disorder and rage responses. The patient was going through such severe crisis that she demanded that a trial of Tegretol be initiated as quickly as a CBC could be obtained with a promise to obtain an EEG at a later date after Tegretol had been discontinued for at least 72 hours. Tegretol was increased to therapeutic dosages. Immediately thereafter the patient was calmer. In the interim, the patient went to have a procaine activated EEG which was positive. The patient was finally stabilized on 200 mgm of Tegretol three times per day.

EXAMPLE IV

A woman first seen in 1975 with a two year history of depression with anxiety, irritability, lethargy, difficulty in falling asleep and with sleep continuity. She had become addicted to sedatives and alcohol in her efforts to obtain sleep. Despite these symptoms, she had been able to function as a mother and wife.

She was initially treated with Amitriptyline but suffered a hypomanic episode requiring hospitalization. During the hospital stay, she was started on lithium carbonate and thioridazine but soon required an antidepressant. Over the course of the next five years, she was maintained on lithium and thioridazine (intermittently) with a series of TCA's (protriptyline, imipramine, doxepin and nortriptyline). Both the lithium and thioridazine were discontinued at this point and she was started on Bupropion, first during a study and subsequently under a humanitarian IND. Much of her depressive symptomatology cleared though she continued to experience mild lethargy, irritability and considerable sleep difficulty. She did not experience as much mood improvement as on the TCA's but on the Bupropion was able to lose the weight she had gained on the previous medications. During this period, she entered insight oriented psychotherapy and intermittent marital counselling with considerable success.

During the course of therapy it was learned that the patient had some learning difficulties in childhood and still had auditory perceptual problems for which she had compensated. Because of this history, her continuing mood disorder (albeit milder), despite antidepressant, lithium and neuroleptic treatment, further evaluation was conducted. Neuropsychological testing demonstrated a mild disturbance in tactile and auditory perception. An EEG showed bursts of moderate voltage slow waves, often sharply contoured in the left anterior temporal area, intensified with hyperventilation. Subsequently she was started on carbamazepine and improved considerably though continued to be depressed. Wellbutrin was added to the regimen and the depression cleared. After two years the Wellbutrin was discontinued. The patient has remained on carbamazepine and continues to feel well and function well fourteen years after her initial contact.

The daughter of the prior case was brought in a few months after her mother was started on carbamazepine. She had a history of learning problems, poor school performance, decreased attention span, irritability, negativism and considerable anxiety. Neuropsychological testing showed poor spatial reasoning and decreased auditory perception. An EEG showed no irregularities. However, a procaine challenge produced a positive response with omega activity in the anterior temporal areas bilaterally. She was placed on carbamazepine and improved moderately but continued to experience some irritability, mild mood swings and decreased concentration. An antidepressant was added and she became asymptomatic. Five years later, she continues to be asymptomatic, has completed her first year of college with good grades and has been socially active. Repeat neuropsychological testing one year after the first test showed little perceptual difficulty and general improvement.

EXAMPLE V

A male who presented with a history of depression since childhood, marked by a general negativism, easy fatiguability, constant anxiety, irritability, sleep disturbance, and recurrent suicidal ideation. He had been chronically alcoholic for a ten year period until 1½ years prior to being seen by one of the present inventors when he stopped and joined AA. During this 1½ year period, his depressive symptomology intensified. There was an extensive family history of alcoholism and a suggestive, though not definitive, history of depression.

He was started on Desipramine at an adequate dose as judged by plasma levels and improved partially though remaining suicidal. Because of the partial effectiveness and adverse effects, he was tried on two other TCA's before being placed on Bupropion. There was some additional improvement but it was recognized that the patient had been experiencing seasonal mood change with bouts of euphoria followed by periods of deep depression. He was started on lithium and one year later on Trifluoperazine when his cycling had not fully abated and his anxiety level remained high. There was further improvement but suicidal ideation and some dysphoria continued. An EEG was obtained and showed no abnormalities but there was a positive response to a procaine challenge. Carbamazepine was added to the medication regimen and gradually increased to a level of 9.5 mg/ml. Within two to three months, he became symptom free with no further suicidal ideation. Three years later he has remained symptom free and has completed his training to become an alcoholism counselor.

EXAMPLE VI

Patients presenting with the complete criteria for Attention Deficit Hyperactivity Disorder (ADHD) as defined in DSM III-R, 1987, pp. 56-57. If these patients test procaine negative they will mainly respond with a decrease in the severity of their symptoms or functional impairment to stimulants such as Ritalin or Dexedrine or stimulatory antidepressants such as Desipramine, Imipramine, Wellbutrin or Prozac. If these patients test procaine positive, stimulants or stimulatory antidepressants alone often exacerbate their symptoms and the best response will occur with anticonvulsants alone or with the addition of stimulants or stimulatory antidepressants once the patient has been stabilized on anticonvulsant medication. With adolescents, more consistent, favorable responses are found with Depakote. A more negative hyperactive or agitated response is sometimes seen in adolescents with Tegretol perhaps because it is structurally related to the tricyclic antidepressants.

EXAMPLE VII

Patients presenting with the complete symptom criteria for Panic Disorder as defined in DSM III-R or Panic Attacks as defined previously under symptom group two. If the patient tests procaine positive, attempts to treat with antidepressants alone such as Imipramine, Desipramine, Prozac or Nardil results in either brief limited improvement, no change, or exacerbation of their symptoms. Treatment with anticonvulsants alone or with the addition of antidepressants once the patient has been stabilized on anticonvulsant medication is generally favorable, particularly with Tegretol.

EXAMPLE VIII

Patients presenting with the complete symptom criteria of Cyclothymia or Bipolar Disorder, Mixed as defined in DSM III-R or Mood change as defined previously under symptom group one. If the patient tests procaine positive the patient is more likely to respond to anticonvulsant medication with or without lithium, antidepressants or neuroleptics. If the patient is procaine negative treatment with lithium with or without antidepressant or neuroleptic is suggested.

TABLE I

| AGE | Age and Sex | | |
|---|---|---|---|
| | TOTAL | MALE | FEMALE |
| 10-19 | 4 | 0 | 4 |
| 20-29 | 5 | 1 | 4 |
| 30-39 | 22 | 3 | 19 |
| 40-49 | 16 | 3 | 13 |
| 50-59 | 8 | 3 | 5 |
| 60-69 | 1 | 0 | 1 |
| TOTALS = | 56 | 10 | 46 |

TABLE I-A

| AGE | Age and Sex | | |
|---|---|---|---|
| | TOTAL | MALE | FEMALE |
| 10-19 | 79 | 39 | 40 |
| 20-29 | 14 | 9 | 5 |
| 30-39 | 11 | 5 | 6 |
| 40-49 | 7 | 3 | 4 |
| 50-59 | 2 | 2 | 0 |
| 60-69 | 1 | 1 | 0 |
| TOTALS = | 114 | 59 | 55 |

TABLE II

| EEG Evaluation | | |
|---|---|---|
| | | TEGRETOL RESPONSE |
| ABNORMAL: | | |
| Slowing | 26 | 23 definite |
| | | 3 possible |
| Fast activity | 2 | 2 definite |
| Occasional slowing | 5 | 2 definite |
| | | 3 possible |
| PROCAINE: | | |
| Positive | 15 | 11 definite |
| | | 3 possible |
| | | 1 none |
| Negative | 8 | none |

TABLE II-A

| EEG Evaluation | | |
|---|---|---|
| | | ANTICONVULSANT RESPONSE: |
| ABNORMAL: | | |
| Frequent slowing and/or paroxyomal sharp wave activity | *9 | *6 Yes (1 Procaine +) |
| | | 2 No |
| | | 1 Non-compliant |
| Omega activity without procaine | 4 | 1 Yes |
| | | 1 Yes for 8 months |
| | | 2 No (1 Procaine +) |
| Occasional slowing and/or paroxyomal sharp wave activity | 4 | 2 Yes (Both Procaine +) |
| | | 1 Possible |
| | | 1 No |
| **PROCAINE: | | |
| Positive | 70 | 47 Yes |
| | | 3 Yes but non-compliant |
| | | 13 Yes with adverse side effects changing 6 to another anticonvulsant |
| | | 1 Possible |

TABLE II-A-continued

| EEG Evaluation | | ANTICONVULSANT RESPONSE: | |
|---|---|---|---|
| Negative | 32 | 6 | No |
| | | 2 | Yes |
| | | 28 | No |
| | | 2 | No medication prescribed |

*1 patient had clear spike and wave discharge
**11 patients procaine not done for clinical reasons and 1 patient refused procaine

TABLE III

| Diagnoses - Axis I | |
|---|---|
| Major Depression | 16 |
| Dysthymic Disorder | 10 |
| Panic Disorder | 3 |
| Schizoaffective Disorder | 2 |
| Bipolar Disorder | |
| I | 3 |
| II | 11 |
| III | 9 |
| IV | 2 |
| | 56 = TOTAL |

TABLE III-A

| Diagnoses - Axis I (More than one diagnoses per person possible) | |
|---|---|
| Depressive Disorder, NOS | 47 |
| Dysthymic Disorder | 4 |
| Major Depression | 14 |
| Organic Mood Disorder | 26 |
| Bipolar Disorder | 6 |
| Schizoaffective Disorder | 9 |
| Attention Deficit Disorder | 20 |
| Explosive Disorder | 14 |
| Alcohol Abuse | 3 |
| Substance Abuse | 19 |
| Panic Disorder | 2 |
| Generalized Anxiety | 6 |
| Bulimia | 2 |
| Borderline Personality Disorder | 5 |

What is claimed is:

1. A method for diagnosing a patient to determine whether said patient has Limbic System Dysrhythmia and is susceptible of being treated by being administered an anticonvulsant medication which method comprises diagnosing said patient to determine whether said patient exhibits at least four of the twelve groups of symptoms selected from the group consisting of mood change, panic attacks, rage reaction, headaches, addictive states, learning disability, paranoid episodes or thinking, peripheral neuropathic signs, seizure-like phenomena, self-destructive behavior, autoimmune-endocrine disorders and antidepressant stimulant response; performing on said patient at least one test selected from the group consisting of:
    (a) An electroencephalographic test employing anteriortemporal leads, and analyzing the results of said electroencephalographic test looking for the condition of focal abnormalities in the temporal-parietal areas; and,
    (b) Administering a local anaesthetic intravenously to said patient, then performing an electroencephalographic test employing anterior-temporal leads, and analyzing the results of said electroencephalographic test looking for the condition of omega activity (30-50 Hz.) of at least approximately three times the baseline voltage in the anterior-temporal leads and, if the patient exhibits symptoms in at least four groups of said twelve groups of symptoms and exhibits at least one of the above conditions in (a) or (b) said patient is diagnosed as having Limbic System Dysrhythmia and is susceptible of being treated with an anticonvulsant medication.

2. The method of claim 1 wherein said local anaesthetic is procaine.

3. The method of claim 1 which further comprises intravenously administering to said patient a local anaesthetic at a dosage of about 1.38 mg/kg of body weight in a volume of about 3-6 cc prior to performing said electroencephalographic test on said patient.

4. The method of claim 1 wherein said omega activity of at least approximately three times the baseline voltage is at least about 45 microvolts.

5. A method for treating a patient suffering from mental disorder which comprises diagnosing said patient to determine whether said patient has Limbic System Dysrhythmia and is susceptible of being treated by being administered an anticonvulsant medication by diagnosing said patient to determine whether said patient exhibits symptoms in at least four groups of the twelve groups of symptoms consisting of mood change, panic attacks, rage reaction, headaches, addictive states, learning disability with or without symptoms of ADHD, paranoid episodes or thinking, peripheral neuropathic signs, seizure-like phenomena, self-destructive behavior, autoimmune endocrine disorders and antidepressant stimulant response; performing on said patient at least one test selected from the group consisting of:
    (a) An electroencephalographic test employing anteriortemporal leads, and analyzing the results of said electroencephalographic test looking for the condition of focal abnormalities in the temporal-parietal areas; and,
    (b) Administering a local anaesthetic intravenously to said patient, then performing an electroencephalographic test employing anterior-temporal leads, and analyzing the results of said electroencephalographic test looking for the condition of omega activity (30-50 Hz.) of at least about three times baseline voltage in the anterior-temporal leads and, if the patient exhibits symptoms in at least four groups of said twelve groups in at least four of said 12 groups and exhibits at least one of the above conditions in (a) or (b) said patient is diagnosed as having Limbic System Dysrhythmia and is susceptible of being treated with an anticonvulsant medication; and administering an anticonvulsant medication to said patient.

6. The method of claim 5 wherein said local anaesthetic is procaine.

7. The method of claim 5 which comprises intravenously administering to said patient a local anaesthetic at a dosage of about 1.38 mg/kg of body weight in a volume of about 3-6 cc prior to performing said electroencephalographic test on said patient.

8. The method of claim 5 wherein said anticonvulsant is carbamazepine.

9. The method of claim 5 wherein said anticonvulsant is valproic acid.

10. The method of claim 5 wherein said anticonvulsant is klanazepam.

11. The method of claim 5 which further comprises administering an antidepressant of neuroleptic medication in addition to said anticonvulsant to treat said Limbic System Dysrhythmia.

12. The method of claim 5 wherein said omega activity of at least approximately three times the baseline voltage is at least about 45 microvolts.

* * * * *